(12) United States Patent
Rao et al.

(10) Patent No.: US 10,099,199 B2
(45) Date of Patent: Oct. 16, 2018

(54) REACTIVE SCRUBBING FOR UPGRADING PRODUCT VALUE, SIMPLIFYING PROCESS OPERATION AND PRODUCT HANDLING

(71) Applicant: Gas Technologies LLC, Walloon Lake, MI (US)

(72) Inventors: Krishna K. Rao, The Woodlands, TX (US); Evan Michael Visser, Hull, IA (US); Ian Lawrence Gaffney, Los Gatos, CA (US); Walter Breidenstein, Boyne Falls, MI (US)

(73) Assignee: GAS TECHNOLOGIES LLC, Walloon Lake, MI (US)

( * ) Notice: Subject to any disclaimer, the term of this patent is extended or adjusted under 35 U.S.C. 154(b) by 85 days.

(21) Appl. No.: 14/922,623

(22) Filed: Oct. 26, 2015

(65) Prior Publication Data

US 2016/0045890 A1     Feb. 18, 2016

Related U.S. Application Data

(62) Division of application No. 13/841,975, filed on Mar. 15, 2013, now Pat. No. 9,174,903.

(51) Int. Cl.
| | |
|---|---|
| *B01J 19/24* | (2006.01) |
| *C07C 29/80* | (2006.01) |
| *C07C 29/86* | (2006.01) |
| *B01J 12/00* | (2006.01) |
| *C07C 45/35* | (2006.01) |
| *C07C 45/33* | (2006.01) |

(52) U.S. Cl.
CPC .............. *B01J 19/245* (2013.01); *B01J 12/00* (2013.01); *C07C 29/80* (2013.01); *C07C 29/86* (2013.01); *B01J 2219/24* (2013.01); *C07C 45/33* (2013.01); *C07C 45/35* (2013.01)

(58) Field of Classification Search
CPC ...... B01J 12/00; B01J 19/245; B01J 2219/24; C07C 29/80; C07C 29/86; C07C 45/33; C07C 45/35
See application file for complete search history.

(56) References Cited

U.S. PATENT DOCUMENTS

| | | |
|---|---|---|
| 2,004,714 A | 6/1935 | Thompson et al. |
| 2,130,080 A | 9/1938 | Evans |
| 2,376,668 A | 5/1945 | Derby et al. |
| 2,977,386 A | 3/1961 | Kise et al. |
| 3,282,983 A | 11/1966 | Lachowicz et al. |
| 4,065,421 A | 12/1977 | Allyn et al. |
| 4,276,055 A | 6/1981 | Huang |
| 4,417,903 A | 11/1983 | Hinkamp |
| 4,541,835 A | 9/1985 | Norton et al. |
| 4,541,837 A | 9/1985 | Norton et al. |
| 4,603,662 A | 8/1986 | Norton et al. |
| 4,618,451 A | 10/1986 | Gent |
| 4,760,210 A | 7/1988 | Sweeney |
| 4,833,171 A | 5/1989 | Sweeney |
| 5,177,114 A | 1/1993 | Van Dijk et al. |
| 5,520,710 A | 5/1996 | Olah |
| 5,628,805 A | 5/1997 | Lif et al. |
| 6,013,114 A | 1/2000 | Hille et al. |
| 6,255,357 B1 | 7/2001 | Abbott |
| 6,270,541 B1 | 8/2001 | Basu et al. |
| 6,486,362 B1 | 11/2002 | Forestiere et al. |
| 6,514,299 B1 | 2/2003 | Bean et al. |
| 6,548,681 B1 | 4/2003 | Chopade et al. |
| 6,599,336 B2 | 7/2003 | Hamada |
| 6,846,951 B1 | 1/2005 | Thiebaut |
| 7,005,529 B2 | 2/2006 | Eek-Vancells |
| 7,456,327 B2 | 11/2008 | Pawlak et al. |
| 7,470,811 B2 | 12/2008 | Thiebaut |
| 7,578,981 B2 | 8/2009 | Pawlak et al. |
| 7,614,085 B2 | 11/2009 | Schwab et al. |
| 7,642,293 B2 | 1/2010 | Pawlak et al. |
| 7,687,669 B2 | 3/2010 | Pawlak et al. |
| 7,846,978 B2 | 12/2010 | Olah et al. |
| 7,879,296 B2 | 2/2011 | Pawlak et al. |
| 7,910,787 B2 | 3/2011 | Pawlak et al. |

(Continued)

FOREIGN PATENT DOCUMENTS

| | | |
|---|---|---|
| EP | 0 407 038 B1 | 1/1995 |
| WO | 2008-135801 A2 | 11/2008 |

OTHER PUBLICATIONS

Kiernan, "Formaldehyde, Formalin, Paraformaldehyde and Glutaraldehyde: What They Are and What They Do," Microcopy Today, 00-1 pp. 8, 10 and 12, 2000. pp. 9 and 11 are omitted because they are advertisements. (Year: 2000).*
U.S. Appl. No. 15/660,149, filed Jul. 26, 2017, Gaffney et al., 12 pages.
International Search Report dated Jul. 2, 2014 in PCT/US2014/028368, filed Mar. 14, 2014, 6 pgs.
International Search Report dated Jul. 29, 2014 in PCT/US2014/028368, filed Mar. 14, 2014, 4 pgs.
International Search Report dated Aug. 22, 2014 in PCT/US2014/030161, filed Mar. 17, 2014, 4 pgs.

(Continued)

*Primary Examiner* — Pancham Bakshi
*Assistant Examiner* — Mark R Luderer
(74) *Attorney, Agent, or Firm* — Brooks Kushman P.C.

(57) ABSTRACT

An apparatus for removing formaldehyde from a blend of partially oxygenated hydrocarbons includes a reactor for reacting a hydrocarbon-containing gas with an oxygen-containing gas in a reactor vessel to form first product blend. The first product blend includes a blend of partially oxygenated compounds that include formaldehyde. The apparatus also includes a reactive scrubbing station in fluid communication with the reactor where the blend of partially oxygenated compounds that include formaldehyde is contacted with a reactive scrubbing liquid at the reactive scrubbing station to form a reactive liquid-formaldehyde compound.

4 Claims, 1 Drawing Sheet

(56) References Cited

U.S. PATENT DOCUMENTS

| | | |
|---|---|---|
| 8,148,589 B2 | 4/2012 | Gracey et al. |
| 8,193,254 B2 | 6/2012 | Pawlak et al. |
| 8,202,916 B2 | 6/2012 | Pawlak et al. |
| 8,293,186 B2 | 10/2012 | Pawlak et al. |
| 8,410,183 B2 | 4/2013 | Cortright et al. |
| 9,174,903 B2 | 11/2015 | Rao et al. |
| 9,255,051 B2 | 2/2016 | Gaffney et al. |
| 9,587,189 B2 | 3/2017 | Gaffney et al. |
| 2002/0026744 A1 | 3/2002 | Golubkov et al. |
| 2006/0204413 A1* | 9/2006 | Pawlak .............. C07C 29/50 422/198 |
| 2006/0223892 A1 | 10/2006 | Pawlak et al. |
| 2007/0100005 A1 | 5/2007 | Pawlak et al. |
| 2007/0130822 A1 | 6/2007 | Araya |
| 2009/0048468 A1 | 2/2009 | Varkiani et al. |
| 2009/0069607 A1 | 3/2009 | Smith, Jr. et al. |
| 2010/0041776 A1 | 2/2010 | Czernichowski et al. |
| 2010/0158760 A1 | 6/2010 | Pawlak et al. |
| 2010/0242347 A1 | 9/2010 | Eberhard |
| 2011/0040129 A1 | 2/2011 | Loescher |
| 2012/0142973 A1 | 6/2012 | Su et al. |
| 2012/0232311 A1 | 9/2012 | Hsieh et al. |
| 2013/0035519 A1 | 2/2013 | Lee et al. |
| 2014/0275643 A1 | 9/2014 | Rao et al. |
| 2016/0031780 A1 | 2/2016 | Gaffney et al. |
| 2016/0045890 A1 | 2/2016 | Rao et al. |
| 2017/0145329 A1 | 5/2017 | Gaffney et al. |
| 2017/0320801 A1 | 11/2017 | Gaffney et al. |

OTHER PUBLICATIONS

International Search Report dated Jan. 8, 2015 in PCT/US2014/058628, filed Jan. 1, 2015, 4 pgs.

Nunan, J.G. et al., "Methanol and 2-Methyl-1-Propanol (Isobutanol) Coupling to Ethers and Dehydration over Nafion H: Selectivity, Kinetics and Mechanism," J. of Catalysis 139, pp. 406-420 (1993).

Zhang, X. et al., "Synthesis of Methylal by Catalytic Distillation," Chemical Engineering Research and Design 89, pp. 573-580 (2011).

* cited by examiner

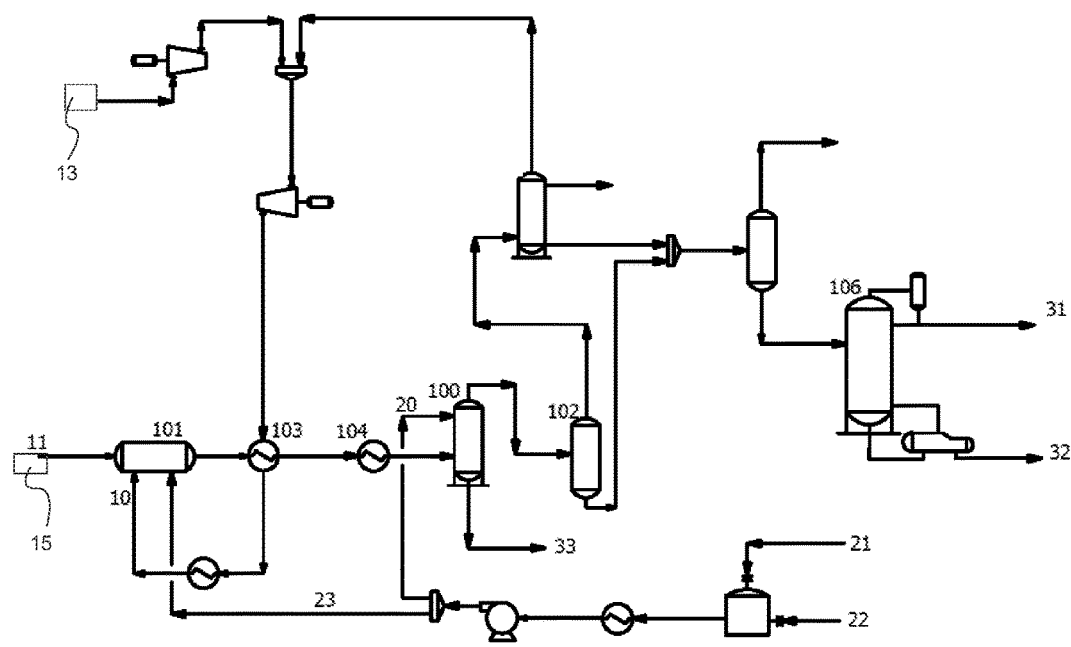

REACTIVE SCRUBBING FOR UPGRADING PRODUCT VALUE, SIMPLIFYING PROCESS OPERATION AND PRODUCT HANDLING

CROSS-REFERENCE TO RELATED APPLICATIONS

This application is a division of U.S. application Ser. No. 13/841,975 filed Mar. 15, 2013, now U.S. Pat. No. 9,174,903 issued Nov. 3, 2015, the disclosure of which is hereby incorporated in its entirety by reference herein.

TECHNICAL FIELD

In at least one aspect, the present invention relates to methods and equipment for removing formaldehyde from partially oxidized hydrocarbons.

BACKGROUND

Methane conversion to methanol is currently in commercial operation worldwide and the classic standard technology practiced is via total oxidation using catalysts. These operations are very capital intensive, require huge pockets of methane gas and the methanol is produced through a syngas route. In addition to the need for huge capital and gas reserves, there is a large amount of carbon dioxide produced that contributes to a significant wastage of oxygen and methane itself.

In order to overcome the process inefficiencies, the capital intensity and the need for huge gas reserves, an alternative process, namely partial oxidation has emerged and has been documented. This partial oxidation non-catalytic route produces valuable products: alcohols (predominantly methanol and ethanol along with higher alcohols) and aldehydes (namely formaldehyde).

Separation to recover methanol, ethanol and formaldehyde is straightforward, involves a distillation process operation and can be accomplished either in batch or continuous manner. The processing steps involve fractionating methanol and the ethanol azeotrope (95% ethanol) as two distinctive fractionating cuts, leaving behind a heel of aqueous formaldehyde (formalin) at the bottom of the still. The ethanol azeotrope is further purified to ethanol using a hydrocarbon such as xylene.

Due to the proximity of boiling points of the aqueous formaldehyde solution with the ethanol azeotrope, special care must be taken to prevent formaldehyde accumulation in the distillate while maximizing ethanol recovery. By reacting formaldehyde to different chemicals, eg urea-formaldehyde, the boiling point can be modified and separation processes simplified.

Formaldehyde is a gas at standard temperature and pressure, for this reason it is typically transported as an aqueous formaldehyde solution composed of 37% formaldehyde by weight. However, although it is encountered in a liquid solution, the formaldehyde molecule is still present and is classified as carcinogenic by the Occupational Safety and Health Association. Direct integration of the synthesis of different chemicals using formaldehyde as a feedstock within the gas-to-chemicals process facilitates product handling, eliminates toxicity issues and further permits generation of higher value products.

Accordingly, there is a need for improved methods of removing aldehydes and in particular formaldehyde from the partially oxygenated hydrocarbons.

SUMMARY

The present invention solves one or more problems of the prior art by providing in at least one aspect a method and apparatus using reactive scrubbing mediums to remove formaldehyde that is formed during the partial oxidation of hydrocarbons without altering the methanol and ethanol components that are coproduced during the non-catalytic partial oxidation. Reactive Scrubbing implies using a media to react with a molecule to form a newer molecule that will exhibit its own properties different from the original molecule.

In another aspect, a method for removing formaldehyde from a blend of partially oxygenated hydrocarbons is provided. The method includes a step of reacting a hydrocarbon-containing gas with an oxygen-containing gas in a reaction vessel to form the first product blend. The first product blend includes a blend of partially oxygenated compounds that include formaldehyde. The blend of partially oxygenated compounds is provided to a reactive scrubbing station where it is contacted with a reactive scrubbing liquid to form a reactive liquid-formaldehyde compound. The reactive liquid-formaldehyde compound is then removed from the first blend of partially reactive compounds.

In another aspect an apparatus for removing formaldehyde from a blend of partially oxygenated hydrocarbons is provided. The apparatus includes a reactor for reacting a hydrocarbon-containing gas with an oxygen-containing gas in a reactor vessel to form first product blend. The first product blend includes a blend of partially oxygenated compounds that include formaldehyde. The apparatus also includes a reactive scrubbing station in fluid communication with the reactor where the blend of partially oxygenated compounds that include formaldehyde is contacted with a reactive scrubbing liquid at the reactive scrubbing station to form a reactive liquid-formaldehyde compound.

BRIEF DESCRIPTION OF THE DRAWINGS

FIGURE is a schematic illustration of a system for removing formaldehyde from a partially oxidized hydrocarbon.

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

With reference to the FIGURE, a schematic illustration of an apparatus for converting gas to hydrocarbons to a partially oxidized product with subsequent reactive scrubbing is provided. The process both sequesters the formaldehyde product and converts it to a less toxic, higher-value product. In a refinement, the apparatus functions in a continuous manner when in operation. The apparatus includes scrubbing vessel 100 for performing reactive scrubbing. Gas phase partial oxidation which generates the liquid products is performed in a reactor 101 which is supplied with a hydrocarbon-containing gas 10 and an oxygen-containing gas 11. In a refinement, the reaction is operated at pressures from about 450 to 1250 psia and temperatures from about 350 to 450° C. In a refinement, reactor 101 is in fluid communication with vessel 100 via one or more conduits and stations interposed therein. Hydrocarbon-containing gas 10 and an oxygen-containing gas 11 react to form the first product blend which is a blend (i.e., a mixture) of partially oxygenated compounds that include formaldehyde. In a refinement, the first product blend includes $C_{1-10}$ alcohols and/or $C_{1-5}$ aldehydes. In another refinement, the first product blend includes an alcohol selected from the group consisting of methanol, ethanol, propanols, butanols, pentanols and combinations thereof, and/or aldehyde selected from the group consisting formaldehyde, acetaldehyde, propionaldehyde and combinations thereof. In another refinement, the first product blend includes an alcohol selected from the group consisting of methanol, ethanol, and combinations thereof, and aldehyde selected from the group consisting formaldehyde, acetaldehyde, and combinations thereof. Examples of systems and methods of performing the partial oxidation as set forth in U.S. Pat. Nos. 8,293,186; 8,202,916; 8,193,254; 7,910,787; 7,687,669; 7,642,293; 7,879,296; 7,456,327; and 7,578,981; the entire disclosures of which are hereby incorporated by reference. In a refinement, the hydrocarbon-containing gas includes $C_{1-10}$ alkanes. In another refinement, the hydrocarbon-containing gas includes an alkane selected from the group consisting of methane, ethane, propanes, butanes, pentanes and combinations thereof. In another refinement, the hydrocarbon-containing gas includes an alkane selected from the group consisting of methane, ethane, and combinations thereof. Examples of oxygen containing gas include molecular oxygen which may be in the form of concentrated oxygen or air.

Following partial oxidation reaction the reactant stream is rapidly cooled in a series of heat exchangers 103 and 104 to prevent decomposition of the produced oxygenates and for separation of the liquid fraction. In the absence of reactive scrubbing the alcohols and aldehydes are condensed and separated in a liquid-gas separator 102. The raw liquid stream composed predominantly of methanol, ethanol and formaldehyde is then separated via fractional distillation 106 in which methanol and ethanol 31 are first separated from the formaldehyde/water solution (formalin) 32 and these two streams may be further processed to obtain the desired purity.

Non-converted hydrocarbon gas exiting the liquid-gas separator 102 is submitted to separation techniques for removal of undesirable non-hydrocarbon fractions which may include but are not limited to scrubbing, membrane separation, adsorption processes, cryogenic separations, or by purging a small gas fraction. The hydrocarbon gases are then recycled back to the reactor 101 with the intent of maximizing efficiency of the process.

In a variation of the present invention, a reactive scrubbing vessel 100 may be located upstream of the gas-liquid separation vessel 102 so as to maintain a higher temperature to favor reactive scrubbing. A reactive scrubbing liquid 20 (e.g. urea) is added to the reactive scrubbing vessel. The scrubbing liquid is designed to react with one or multiple fractions of the gas stream to generate higher-valued products, such as urea-formaldehyde. The reactive liquid also facilitates downstream fractional distillation due to the different boiling points of the synthesized products.

The reactive scrubbing liquid is generated by diluting the reactive substance 21 (e.g., urea) in water 22 which may be obtained from the partial oxidation process itself. This liquid solution is compressed and injected into the reactive scrubbing vessel 102. Alternatively, liquid stream 23 may be injected into the downstream end of the reactor 101 to both react with a designed product fraction and also to quench the reaction products in order to minimize decomposition of generated oxygenates.

Differences in operating temperatures of the reactive scrubber 100 and gas-liquid separator 102 facilitate separation schemes. Alcohols are sparingly soluble in urea at temperatures exceeding 100° C. in the reactive scrubber alcohols will remain in a gaseous state to be recovered in the gas-liquid separator 102. Formaldehyde reacting with the urea solution will be found as a liquid solution 33 in the bottom of the reactive scrubber 100 and be separated from both the gas and alcohol fractions. For reactive scrubbing at lower temperatures at which alcohols may condense, simple distillation procedures permit separation of alcohols from reactive scrubbing products (e.g., urea-formaldehyde). In a refinement, the scrubber is operated at pressures from about 450 to 1250 psia and temperatures from about 50 to 90° C.

While exemplary embodiments are described above, it is not intended that these embodiments describe all possible forms of the invention. Rather, the words used in the specification are words of description rather than limitation, and it is understood that various changes may be made without departing from the spirit and scope of the invention.

Additionally, the features of various implementing embodiments may be combined to form further embodiments of the invention.

What is claimed is:

1. An apparatus for removing formaldehyde from partially oxygenated compounds, the apparatus comprises:
   a) a reactor for reacting a hydrocarbon-containing gas with an oxygen-containing gas in a reactor vessel to form first product blend, the first product blend including a blend of partially oxygenated compounds that include formaldehyde; and
   b) a reactive scrubbing station in fluid communication with the reactor where the first product blend is contacted with a reactive scrubbing liquid at the reactive scrubbing station to form a reactive liquid-formaldehyde compound.

2. The apparatus of claim 1 further comprising an oxygen-containing compound supply and a hydrocarbon supply.

3. The apparatus of claim 1 further comprising a fractional distiller for removing methanol and ethanol from the first product blend that is depleted of formaldehyde.

4. The apparatus of claim 1 further wherein the reactive scrubbing liquid including urea.

\* \* \* \* \*